United States Patent [19]

Nelson

[11] Patent Number: 4,957,908

[45] Date of Patent: Sep. 18, 1990

[54] CHITOSAN PYRITHIONE AS ANTIMICROBIAL AGENT USEFUL IN PERSONAL CARE PRODUCTS

[75] Inventor: John D. Nelson, Naugatuck, Conn.

[73] Assignee: Olin Corporation, Cheshire, Conn.

[21] Appl. No.: 461,720

[22] Filed: Jan. 8, 1990

[51] Int. Cl.$^5$ .................... A61K 31/00; C07D 211/00; C07D 213/00; C08B 37/00

[52] U.S. Cl. ....................................... 514/55; 514/844; 514/847; 514/846; 546/290; 546/292; 536/20; 536/55.2; 536/55.3

[58] Field of Search ................. 536/20, 55.2, 55.3; 514/55, 844, 846, 847; 546/290, 298, 292, 6; 604/358, 360, 364

[56] References Cited

U.S. PATENT DOCUMENTS

| | | | |
|---|---|---|---|
| 3,879,376 | 4/1975 | Vanlerberghe et al. | 536/20 |
| 3,953,608 | 4/1976 | Vanlerberghe et al. | 536/20 |
| 4,048,181 | 9/1977 | Douglass | 546/292 |
| 4,122,084 | 10/1978 | Douglass | 546/6 |
| 4,122,085 | 10/1978 | Douglass | 546/6 |
| 4,345,080 | 8/1982 | Bolich | 546/6 |
| 4,528,283 | 7/1985 | Lang et al. | 536/20 |
| 4,533,736 | 8/1985 | Trotz et al. | 546/290 |
| 4,632,991 | 12/1985 | Maurer et al. | 546/6 |
| 4,659,700 | 4/1987 | Jackson | 514/55 |
| 4,659,830 | 4/1987 | Maurer et al. | 546/6 |
| 4,670,430 | 6/1987 | Imamura et al. | 546/6 |
| 4,845,204 | 7/1989 | Lang et al. | 536/20 |

*Primary Examiner*—Ronald W. Griffin
*Assistant Examiner*—Everett White
*Attorney, Agent, or Firm*—Dale Lynn Carlson

[57] ABSTRACT

In accordance with the present invention, a new pyrithione salt, namely chitosan pytighione, is produced. This composition is characterized by a combination of slow release from films and excellent antimicrobial activity. The antimicrobial activity is equivalent to that of sodium pyrithione. These properties make chitosan pyrithione potentially useful as an antimicrobial agent in a variety of dermatological items, such as soaps, shampoos, and skin care medicaments.

5 Claims, No Drawings

CHITOSAN PYRITHIONE AS ANTIMICROBIAL AGENT USEFUL IN PERSONAL CARE PRODUCTS

Chitosan is the deacetylated derivative of the polysaccharide chitin [B-(1-4)-poly-N-acetyl-D-glucosamine], an abundant natural by-product of the crab and shrimp industries. Chitosan is known to be fungicidal for both animal and plant pathogens provided this substance is not a component of the fungal cell wall. Films of chitosan salts have proven useful in healing wounds.

Pyrithione salts, such as zinc and sodium pyrithione which are commercially available under Olin Corporation's registered trademark Omadine ®, are known to have broad antibacterial and antifungal activity. However, because these pyrithione salts are absorbed through the skin fairly rapidly, they may only be used at relatively low concentrations in products intended for topical application. Accordingly, new forms of pyrithione that are more slowly absorbed into the skin would be of significant interest to the skin care industry.

In accordance with the present invention, a new pyrithione salt, namely chitosan pyrithione, is produced. This composition when formed into a film, is characterized by a combination of a slow release of pyrithione and excellent antimicrobial activity. The antimicrobial activity is equivalent to sodium pyrithione. These properties make chitosan pyrithione potentially useful as an antimicrobial agent in a variety of dermatological items, such as soaps, and skin care medicaments.

In accordance with one aspect of the present invention, chitosan pyrithione can be Prepared either by reacting chitosan acetate salt with a pyrithione salt such as sodium Pyrithione, or by neutralization of chitosan, which is a weak base, with a pyrithione acid. The antimicrobial activity of each of these preparations is illustrated in the examPles given below. These and other asPects will become apparent upon reading the following detailed description of the invention.

The molecular weight of commercially available chitosan is about 100,000 to 300,000. Using this reactant, chitosan pyrithione is produced by the addition of pyrithione as described above. The resulting molecular weight of the chitosan pyrithione product is therefore in the range of between about 100,000 and about 500,000, more probably between about 150,000 and about 500,000 if fully-substituted.

The chitosan pyrithione product has many desirable attributes. Pyrithione possesses good antimicrobial activity, and is compatible with components of conventional soaps, shampoos, skin-care medicaments, and the like It is also non-volatile, hydrolytically-stable, thermally-stable, and soluble in water and common organic solvents. Furthermore, it forms no undesirable colors in typical personal care items. Chitosan is also used in cosmetic products.

The chitosan pyrithione is suitably employed in an antimicrobially-effective amount in a desired dermatological or other personal care product. This "antimicrobially-effective amount" is preferably between about 0.1 and 30 weight percent of such chitosan pyrithion ® based upon the total weight of the personal care product.

The following examples are intended to illustrate, but in no way limit, the scope of the present invention.

Example 1

Preparation of Chitosan Pyrithione and Testing of Its Antimicrobial Activity Against Phytophthora Parasitica Chitosan Pyrithione was prepared by dissolving 1% chitosan (crab shell, Sigma) in 1% Omadine acid (pyrithione). The solution was dialyzed extensively against distilled water to remove excess acid. Based on volume before and after dialysis, the final chitosan concentration was estimated to be 0.55%. The pyrithione concentration, determined by a spectrophotometric assay, was 0.29% or approximately 52.7% of the polymer. The pyrithione concentration was slightly higher than the 38.7% expected if the polymer were fully substituted. However, total weight was estimated in this experiment, and this may account for the disparity.

A control solution of chitosan acetate was prepared by dissolving chitosan in 1% acetic acid. After dialysis, the final chitosan acetate concentration was estimated to be 0.9%. Phytophthora zoospore suspensions were mixed with serial dilutions of the chitosan solutions, and after 1 hour contact, plated on corn meal agar. Spores were also examined microscopically for motility. Zoospores remained viable after treatment with 45ppm ohitosan acetate but were killed by 90ppm. In contrast, exposure to only 2.75 ppm chitosan pyrithione killed the zoospores.

Example 2

Determination of Minimum Inhibitory Concentrations (MICs) For Chitosan Pyrithione Against Various Microorganisms Minimum inhibitory concentrations (MIC's) for the solutions Prepared in ExamPle 1 and for sodium Omadine were determined against 8 fungal and 8 bacterial strains as identified in Table 1 below.

The results as presented in Table 1 indicate that chitosan PYrithione demonstrated activity against all of the strains tested. In contrast, chitosan acetate was not effective against the strains tested.

TABLE 1

Activity of chitosan acetate, chitosan pryithione, and sodium pryithione against bacteria and fungi
MICs (in ppms of active moiety)

|  | Source | Chitosan Acetate | Chitosan Pyrithione | Sodium Pyrithione |
|---|---|---|---|---|
| Bacteria | | | | |
| Pseudomonas aeruginosa | cosmetic isolate | >1000 | 363 | 438 |
| Pseudomonas aeruginosa | shampoo isolate | >1000 | 725 | 875 |
| Pseudomonas syringae | ATCC 19310 | >1000 | 12 | 55 |
| Pseudomonas syringae | ATCC 11355 | >1000 | 2 | 3 |
| Enterobacter aerogenes | cosmetic isolate | >1000 | 12 | 109 |
| Staphylococcus aureus | ATCC 6538 | >1000 | 2 | 3 |
| Xanthomonas campestris | ATCC 11551 | >1000 | 22 | 27 |
| Xanthomonas campestris | ATCC 19315 | >1000 | ≦0.08 | ≦0.10 |

TABLE 1-continued

Activity of chitosan acetate, chitosan pryithione, and sodium pryithione against bacteria and fungi MICs (in ppms of active moiety)

| | Source | Chitosan Acetate | Chitosan Pyrithione | Sodium Pyrithione |
|---|---|---|---|---|
| Fungi | | | | |
| Aspergillus niger | ATCC 16404 | >2250 | 12 | 28 |
| Penicillium levitum | ATCC 10464 | >2250 | 0.4 | 0.1 |
| Fusarium oxysporum | ATCC 15643 | >2250 | 91 | 219 |
| Helminthosporum oryzae | ATCC 34393 | >2250 | ≦0.04 | ≦0.05 |
| Glomerella cingulata | ATCC 10593 | >2250 | ≦0.04 | ≦0.05 |
| Alternaria solani | ATCC 11078 | >2250 | 0.4 | 0.5 |
| Rhizoctonia solani | ATCC 28268 | >2250 | ≦0.04 | ≦0.05 |
| Candida albicans | ATCC 10231 | >2250 | 2 | 0.5 |

Example 3

Antifungal Activity of Chitosan Pyrithione and Chitosan Acetate Films

Chitosan pyrithione and chitosan acetate were prepared as in Example 1 and filter sterilized. Based on a dry weight of 1-2 ml. of material, the chitosan acetate concentration was 0.7%, and the chitosan pyrithione concentration was 0.96%. The pyrithione concentration constituted 21.5% of the chitosan pyrithione Preparation, as determined by spectrophotometric assay.

Ten microliters of the solutions were spread on sterile 22 mm square glass coverslips and air-dried at room temperature to form a film. Coverslips were placed on Mycophil agar (BBL) plates and sprayed with a suspension of *Aspergillus niger* spores. Untreated coverslips were included as controls. Plates were incubated at 28° C. After 90 days, controls and chitosan acetate coated coverslips were overgrown by A. niger, and germinated spores were observed. The chitosan Omadine film repelled fungal growth (Table 2).

TABLE 2

| Qualitative activity of chitosan films against *Aspergillus niger* | | | |
|---|---|---|---|
| Incubation Time (28° C.) | Control (no film) | Chitosan Acetate | Chitosan Omadine |
| 2 days | Confluent growth around coverslip, overgrowth and some germinated spores on coverslip | Same as control | Inhibition around coverslip; no growth on coverslip |
| 9 days | Germinated spores on coverslip | Germinated spores on coverslip | Confluent growth around coverslip; no germinated spores on coverslip. |

Example 4

Preparation of Chitosan Pyrithione by Reacting Chitosan Acetate With Sodium Pyrithione To demonstrate that chitosan pyrithione can be prepared by a method other than by neutralization of pyrithione acid, sodium pyrithione was mixed with chitosan acetate and allowed to eract for several hours before dialysis. After dialysis, the dry weight and pyrithione content of the chitosan pyrithione were determined. Based on dry weight, the solution contained 1.15% substituted polymer, and pyrithione comprised 8.95% of the polymer.

Antifungal activity was demonstrated using two samples of chitosan pyrithione, one prepared by acid neutralization following the procedure of Example 1 and the other by the reaction of salts as described in the preceding paragraph. The samples were spread on glass squares or coverslips and allowed to dry. The squares were placed on Mycophil agar (BBL) plates and overlaid with Mycophil agar inoculated with the fungus *Candida albicans*. Chitosan acetate films and untreated glass squares or coverslips were included as controls. Growth of the test organism was inhibited to a similar extent by both chitosan pyrithione preparations but not by the controls.

In the second type of experiment, 10 ul of each solution was pipetted onto 0.25 inch filter paper disks and allowed to dry. A control solution of aqueous sodium Omadine was included. Treated disks were placed on Mycophil agar plates seeded with *C. albicans*. After incubation, zones of inhibition were measured. Both chitosan pyrithione solutions inhibited the test strain to the same degree as an equivalent amount of aqueous sodium Omadine. In contrast, chitosan acetate showed no inhibitory effect.

What is claimed is:

1. A personal care product comprising an antimicrobial effective amount of chitosan pyrithione and at least one component selected from the group consisting of soaps, shampoos, skin-care medicaments and cosmetics.

2. The product of claim 1 wherein said chitosan pyrithione is present in an amount of between about 0.1 and about 30 weight percent based upon the total weight of said product.

3. A process for producing chitosan pyrithione which comprises reacting chitosan acetate with sodium Pyrithione in an aqueous medium.

4. The process of claim 3 wherein said chitosan pyrithione has a molecular weight of between about 150,000 and about 500,000.

5. A process for producing chitosan pyrithione by a neutralization reaction which comprises reacting pyrithione acid with chitosan base.

* * * * *